United States Patent [19]
Barber et al.

[11] Patent Number: 5,579,462
[45] Date of Patent: Nov. 26, 1996

[54] USER INTERFACE FOR SPECTROMETER

[75] Inventors: Luther L. Barber, Needham; Mark L. Olson, Framingham; Paul V. Carter, Brighton, all of Mass.

[73] Assignee: Bio-Rad Laboratories, Cambridge, Mass.

[21] Appl. No.: 333,955

[22] Filed: Nov. 3, 1994

[51] Int. Cl.$^6$ .................................................. G06F 15/00
[52] U.S. Cl. ................................................................. 395/140
[58] Field of Search .................................. 395/155, 161, 395/139, 140, 141, 142; 345/113, 134, 135

[56] References Cited

U.S. PATENT DOCUMENTS 5,283,867  2/1994  Bayley et al. ........................... 395/164

OTHER PUBLICATIONS

"Grams/38 Level III Database Operations", Galactic Industries Corporation, 1991–1994.
"Simple yet Powerful", Magnai-IR FT-IR Spectrometers with Omnic Software, (brochure), Nicolet Instrument Corporation, 1992.
"Subtraction", Grams (brochure), Galactic Industries Corporation (Jun., 1992).
"Introducing OMNIC 2" OMNIC2 FT-IR Software, Nicolet Instrument Corporation (1993).
"Nicolet QuickIR+", Nicolet Instrument Corporation (1990).
"Quick IR+ User's Guide, Version 1.0", OMNIC FT-IR Software, Nicolet Instrument Corporation Omnic Software Corp, 1994.

*Primary Examiner*—Phu K. Nguyen
*Attorney, Agent, or Firm*—Townsend and Townsend and Crew LLP

[57] ABSTRACT

A method for graphically forming a difference spectrum from a sample spectrum and a reference spectrum on a computer system includes displaying an initial difference spectrum on the display the initial difference spectrum being equal to the sample spectrum, selecting a data point in the initial difference spectrum, having an associated wave number, with a relative pointing device on the display, moving the data point a measurable amount on the display with the relative pointing device, determining a scaling factor in response to the measurable amount and to a data point in the reference spectrum having the same associated wave number, scaling each data point in the reference spectrum by the scaling factor to form a scaled reference spectrum, determining the difference spectrum between the sample spectrum and the scaled reference spectrum, and displaying at least a portion of the difference spectrum on the display.

14 Claims, 15 Drawing Sheets

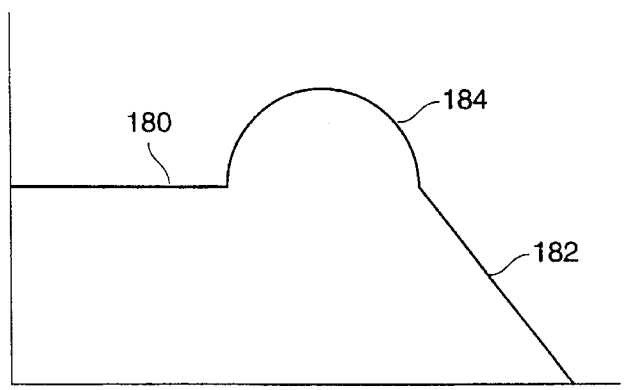
FIG. 10
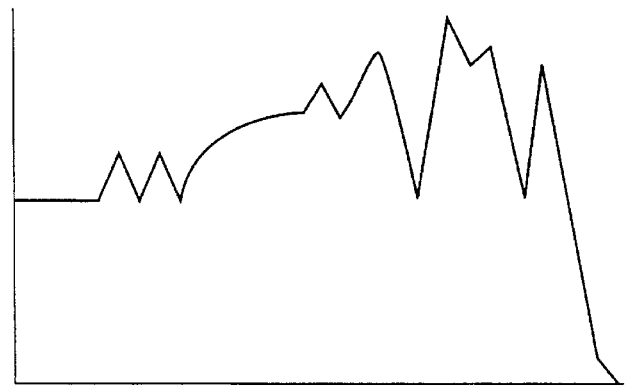
FIG. 11
FIG. 12

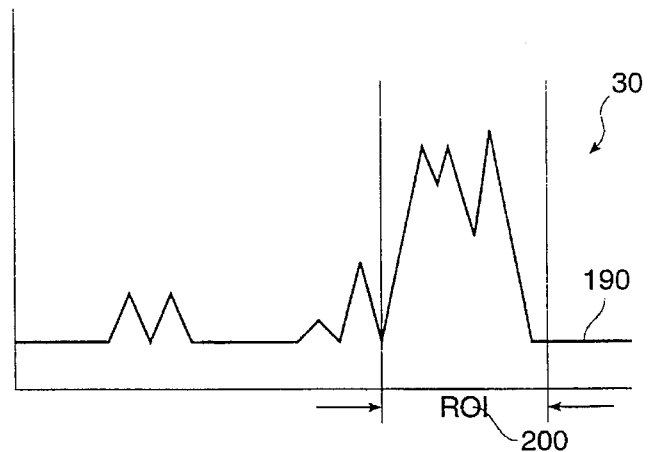
FIG. 13A
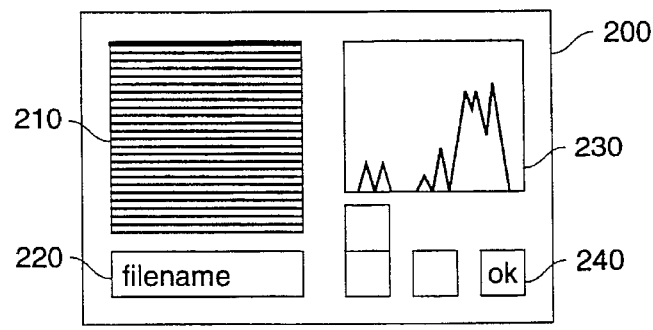
FIG. 13B
FIG. 14
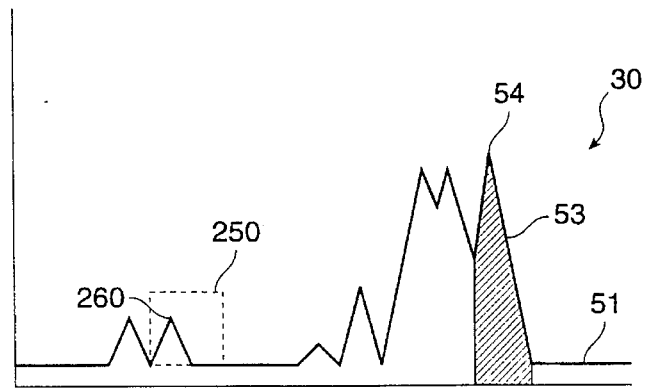
FIG. 15

USER INTERFACE FOR SPECTROMETER

BACKGROUND OF THE INVENTION

The present invention relates generally to graphical display of spectral data, and more specifically to user interface enhancements that facilitate the examination and manipulation of such data.

Spectral analysis is often used to determine the qualitative or quantitative composition of a sample. Typical spectral data consist of the absorbance of the sample or specimen at different wavelengths or frequencies of light. Absorbance data are typically plotted against inverse wavelength (a measure of frequency referred to as wavenumber), with the resulting graph being referred to as a spectrum. Also note that while the discussion of typical usage is appropriately in terms of wavenumber vs. absorbance, many of the same manipulations are applicable to a number of other y units (such as %Transmittance, reflectance, Volts) and x units (such as optical retardation of an interferogram, microns, electron Volts).

In order to interpret spectrum, raw data collected from a sample may require additional manipulations:

(1) Specific sampling techniques affect raw spectral data in known, predictable ways; manipulations can convert the data into a sampling-independent standard form.

(2) Sample preparation and sampling techniques may introduce artifacts, and data manipulations may be applied to correct these.

(3) Many samples are mixtures, and manipulations are required to determine the spectrum and concentrations of the individual compounds present.

In order to eliminate known artifacts and eliminate known components from a sample compound, the data points of the sample spectrum are commonly modified. In one method, each spectral data point in the sample spectrum S, is modified by a corresponding data point representing a known sample compound, in the form of a reference spectrum R. The resulting modified spectrum Z, is related to S and R by equation (1), where a and b are scalar values.

$$Z=S-(a*R)+b \qquad (1)$$

Typically, the user inputs a value for "a" and "b" and the processor calculates the modified spectrum Z. After observing the results of the modified spectrum Z, the user can again modify the values for "a" and "b" and review the new spectrum Z. This process is repeated until the user is satisfied with the appearance of the modified spectrum Z. The same modification process of a sample spectrum is used in determining the composition of the sample or is used in adjusting the baseline offset of the spectrum.

The user often magnifies portions of the sample spectrum to concentrate his analysis. Current systems allow the user the ability to increase or decrease the amount of the spectrum, i.e. the range of wave numbers, that is displayed to the user.

SUMMARY OF THE INVENTION

The present invention provides user interface enhancements in a computerized spectral analysis system that allow the user to directly manipulate spectral representations on the display in a highly intuitive and interactive manner. The user is able, with a pointing device, to directly select a portion of the spectrum for display and to directly perform graphic manipulation of the spectrum, such as spectral subtraction.

According to a preferred embodiment of the invention, a method of displaying a spectrum on a computer system having a display and a graphical input device includes the steps of displaying a reduced size view of the spectrum in a radar window on the display; displaying an overlay window on top of the reduced view; displaying a portion of the spectrum corresponding to the portion of the reduced view bounded by the overlay window in a detailed window on the display; and thereafter displaying a vertically resized overlay window on top of the reduced view in response to input from the graphical input device, the vertically resized window bounding a second portion of the reduced view; and displaying a second portion of the spectrum corresponding to the second portion of the reduced view in the detailed window on the display.

According to another embodiment of the invention, a method for graphically manipulating a sample spectrum on a computer system includes the steps of displaying at least a portion of a difference spectrum on the display, the difference spectrum being the mathematical difference between the sample spectrum and a scaled reference spectrum, the scaled reference spectrum being a reference spectrum scaled by a scaled value; and updating the scaled value in response to graphical manipulation of the difference spectrum by the graphical input device.

Further understanding of the nature and advantages of the invention may be realized by reference to the remaining portions of the specification and drawings. In the drawings, similarly numbered items represent the same or functionally equivalent structure.

BRIEF DESCRIPTION OF THE DRAWINGS

FIG. 10 illustrates the result of searching the sample spectrum in FIG. 2 against a library of known spectrum;

FIGS. 11 and 12 illustrate the definition of a portion of a baseline offset as a function of wavenumber and the resulting spectrum;

FIG. 13A illustrates a display of a portion of a spectrum on a detailed window;

FIG. 13B illustrates the result of an automatic subtraction based upon a region of interest;

FIG. 14 illustrates retrieving a previously scanned sample spectrum from a disk drive;

FIG. 15 illustrates a peak mode and a clipboard window;

DESCRIPTION OF THE PREFERRED EMBODIMENT

System Overview

Figure 1:
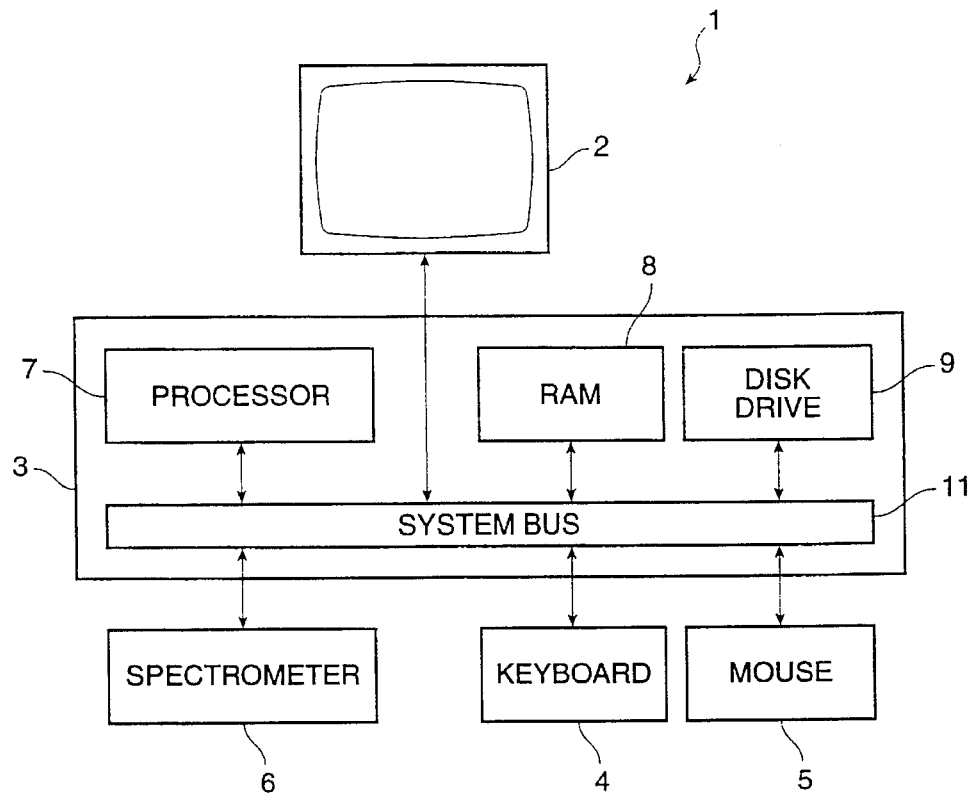
FIG. 1 is a block diagram of a computer system used to execute the present invention.

FIG. 1 is a block diagram of a system 1 according to a preferred embodiment of the present invention. System 1 includes a monitor 2, a computer 3, a keyboard 4, a mouse 5, and a spectrometer 6. Computer 3 includes familiar computer components such as a processor 7, and memory storage devices, such as a random access memory (RAM) 8, a disk drive 9, and a system bus 11 interconnecting the above components. Mouse 5 is but one example of a graphical input device, also known as a pointing device, a trackball is another.

In a preferred embodiment, System 1 includes an IBM PC compatible personal computer, running Windows-NT operating system by Microsoft Corporation and an infra-red spectrometer Model Number FTS 60A from Bio-Rad Laboratories, Inc., and Win-IR Pro software, currently under development by Bio-Rad Laboratories, Inc.

FIG. 1 is representative of but one type of system for embodying the present invention. It will be readily apparent to one of ordinary skill in the art that many system types and configurations are suitable for use in conjunction with the present invention.

Display Overview

Figure 2:
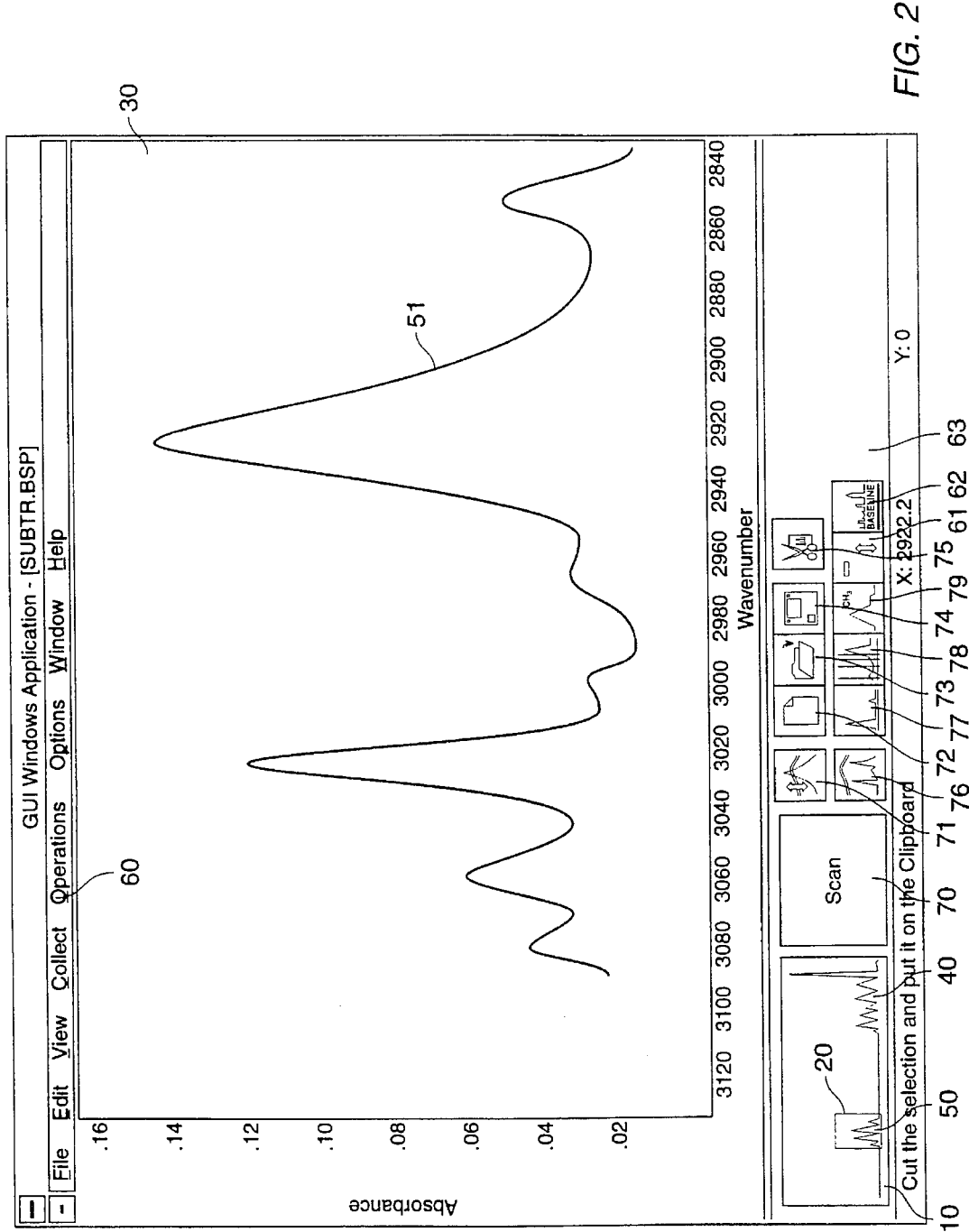
FIG. 2 illustrates one embodiment of the present invention.

FIG. 2 illustrates the display of one embodiment of the present invention, as it would appear on monitor 2. A typical display includes a "radar" window 10 having an overlay window 20, and a detailed window 30. Radar window 10 displays a full range of a spectrum 40, overlay window 20 bounds a portion 50 of spectrum 40, and detailed window 30 displays portion 50 (labeled 51 for convenience). Spectrum 40 is a display of data for a sample spectrum, and can be displayed in a user-selected color.

In accordance with standard user interfaces, a menu bar 60, and command buttons 70–79 and 61–63 are included on the display to provide function capability to the user. Command button 70 is a scan button; command button 71 is a automatic vertical scaling button; command button 72 is a new document button; command button 73 is an open folder; command button 74 is a disk select button; command button 75 is a clipboard button; command button 76 is an automatic ranging button; command button 77 is an overlay window button; command button 78 is a spectrum mask button; command button 79 is a peak mode button; command button 61 is a graphic subtraction mode button; command button 62 is a baseline correction button; and command button 63 is a reference definition button.

In a preferred embodiment, the user first selects command button 70, the scan button, or one of commands in menu bar 60 to initiate scanning of the sample in spectrometer 6. The spectrometer 6 scans a sample (not shown) and processor 7 stores the absorbance data of the sample at different wave numbers in memory 8. The absorbance data versus the wave numbers collectively form the sample spectrum. A sample spectrum can be retrieved from disk drive 9 and loaded into memory 8 by selecting a combination of command buttons 73–74.

Once the data are stored in memory 8 from a scan or from disk drive 9, the processor calculates a spectrum that spans a predefined range of wave numbers or a range of wave numbers having associated absorbance data. This spectrum is then displayed in radar window 10 on the display and denoted the spectrum 40.

In the preferred embodiment, absorbance data is plotted on the vertical axis and wavenumber data is plotted in the horizontal axis.

Next, the processor superimposes overlay window 20 upon radar window 10. The portion of spectrum 40 that is bounded by overlay window 20 defines portion 50. The processor retrieves the spectrum data for portion 50 and displays this data labeled portion 51 in detailed window 30 on the display. Since radar window 10, in one embodiment, occupies a smaller portion of the display than detailed window 30, spectrum 40 is also referred to as a reduced view of the spectrum.

Radar Window Manipulation

Figure 3B:
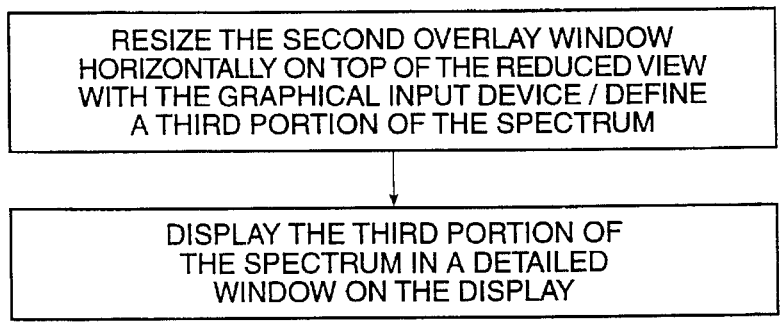
FIG. 3B is a flow diagram of another embodiment of the process of utilizing an overlay window in the radar window.
Figure 3C:
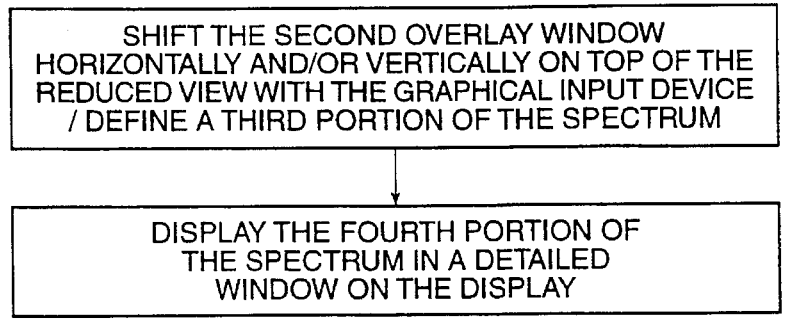
FIG. 3C is a flow diagram of another embodiment of the process of utilizing an overlay window in the radar window.
Figure 3A:
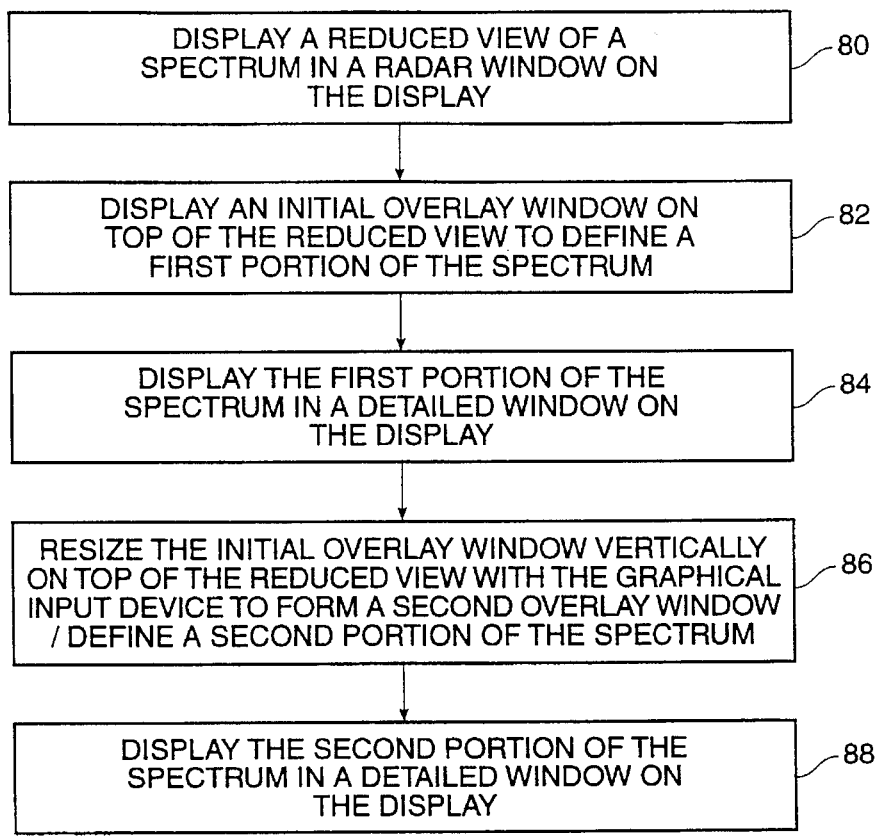
FIG. 3A is a flow diagram of one embodiment of the process and result of utilizing an overlay window in the radar window.

FIG. 3A is a flow diagram of one embodiment of the process and result of utilizing an overlay window in the radar window. A reduced view of spectrum is displayed to the user in the radar window on the display (step 80). The processor generates an initial overlay window in the radar window that bounds and defines a first portion of the spectrum (step 82). The first portion of the spectrum is then displayed to the user in the detailed window (step 84). Using a graphical input device, such as mouse 5, a user vertically resizes the overlay window in the radar window so that the overlay window bounds and defines a second portion of the spectrum (step 86). The second portion of the spectrum is then displayed to the user in the detailed window (step 88).

FIG. 3B is a flow diagram of another embodiment of the process of utilizing an overlay window in the radar window. In addition to steps 80–88 in FIG. 3A, the user may use the graphical input device to horizontally resize the overlay window in the radar window so that the overlay window bounds and defines a third portion of the spectrum (step 90). In this case, the third portion of the spectrum is then displayed to the user in the detailed window (step 92).

FIG. 3C is a flow diagram of another embodiment of the process of utilizing an overlay window in the radar window. In addition to steps 80–88 in FIG. 3A, the user may use the graphical input device to shift the overlay window horizontally and/or vertically in the radar window so that the overlay window bounds and defines a fourth portion of the spectrum (step 94). In this case, the fourth portion of the spectrum is then displayed to the user in the detailed window (step 96).

Figure 4A:
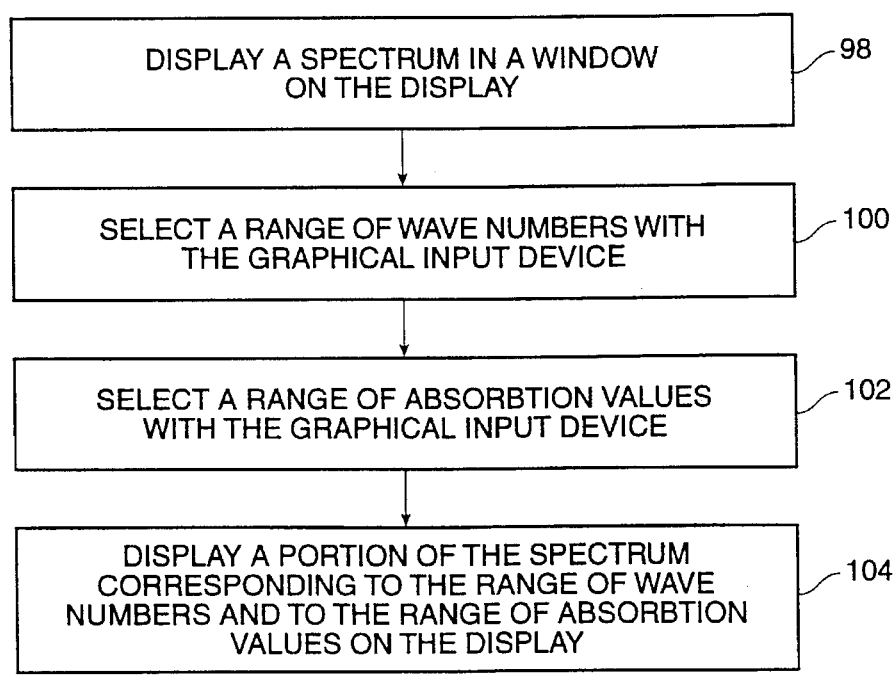
FIG. 4A is a flow diagram of an embodiment of the process of displaying a user-selected portion of a spectrum.

FIG. 4A is a flow diagram of an embodiment of the process of displaying a user-selected portion of a spectrum. A spectrum is first displayed to the user on the display (step 98). The user selects a range of wave numbers with the graphical input device on the display (step 100) and the user selects a range of absorbance values also with the graphical input device on the display (step 102). The user selects the respective ranges with the graphical input device, such as mouse 5, using well known techniques such as clicking upon a base value, and dragging mouse 5 until the desired range is achieved. Once the respective ranges are defined by the user, a portion of the spectrum corresponding to the respective ranges is displayed to the user (step 104).

Figure 4B:
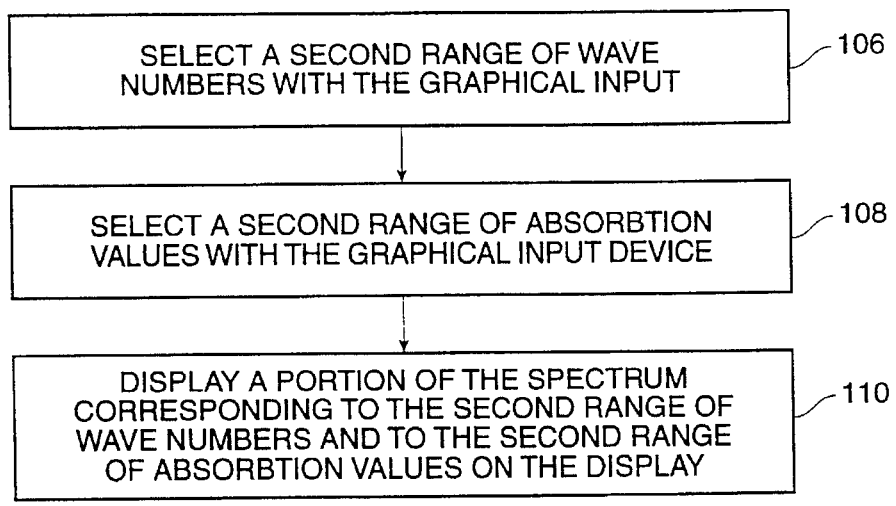
FIG. 4B is a flow diagram of another embodiment of the process of displaying a user-selected portion of a spectrum.

FIG. 4B is a flow diagram of another embodiment of the process of displaying a user-selected portion of a spectrum. In addition to the steps 98–104 in FIG. 4A, the user selects a second range of wave numbers on the display (step 106) and the user selects a second range of absorbance values on the display (step 108), again using well known techniques such as clicking upon a base value, and dragging mouse 5 until the desired range is achieved. Once the respective second ranges are defined by the user, a portion of the spectrum corresponding to the respective second ranges is displayed to the user (step 110).

In a preferred embodiment, the user can "zoom in" on a portion of spectrum 51 by directly defining a region of spectrum 51 in detailed window 30 with the graphical input device in the same manner as overlay window 20. In response, overlay window 20 is updated to reflect the region of the spectrum displayed in detailed window 30.

Figure 5A:
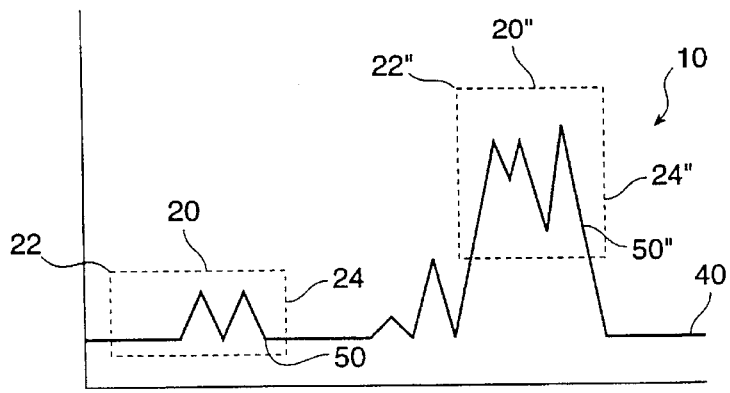
FIG. 5A schematically illustrates moving and stretching of the overlay window on a full spectrum.

FIG. 5A illustrates schematically the moving and stretching of overlay window 20 from a first position to a second position in radar window 10. The overlay window at the second position is denoted 20". Overlay window 20 includes a horizontal side 22 and a vertical side 24, and overlay window 20" includes a horizontal side 22" and a vertical side 24". Overlay window 20 bounds portion 50 and overlay window 20" bounds a portion 5" of the spectrum 40.

In a preferred embodiment, the user employs a graphical input device such as a mouse to manipulate overlay window 20 using well known methods such as pointing, clicking, and dragging a pointer on the display. Specifically with mouse 5, the user independently varies the horizontal location, the vertical location, and the size of overlay window 20 within radar window 10.

The user, clicking the pointer within overlay window 20 and dragging the pointer in the horizontal and vertical direction within radar window 10, shifts the position of overlay window 20 within radar window 10. The shift in the overlay window 20 is reflected in detailed window 30 by the processor displaying different wavenumber data and absorbance data, although the processor maintains the range of wave numbers (horizontal range) and the range of absorbance values (vertical range).

The user, clicking the pointer on vertical side 24 and dragging the pointer in the horizontal direction within radar window 10, increases or decreases the size of horizontal side 22 of overlay window 20 within radar window 10. The change in size of horizontal side 22 is also reflected in detailed window 30 by the processor increasing or decreasing the range of wave numbers displayed in detailed window 30. Similarly, the user clicking the pointer on horizontal side 22 and dragging the pointer in the vertical direction within radar window 10, increases or decreases the size of vertical side 24 of overlay window 20 within radar window 10. The change in size of vertical side 24 is also reflected in the detailed window 30 by the processor increasing or decreasing the range of absorbance values displayed in detailed window 30.

Figure 5B:
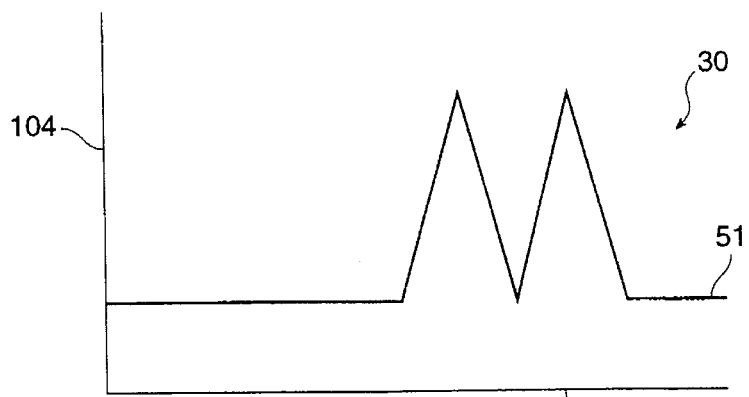
FIG. 5B schematically illustrates the detailed window corresponding to the overlay window at a first position in FIG. 5A.

FIG. 5B illustrates schematically detailed window 30 corresponding to overlay window 20 in FIG. 5A. Detailed window 30 includes a horizontal scale 102 representing a range of wave numbers, a vertical scale 104 representing a range of absorbance values, and portion 51 of spectrum 40.

In operation, overlay window 20 on spectrum 40 defines portion 50 of spectrum 40. Based upon the size of horizontal side 22 and the size of vertical side 24 of FIG. 5A, the processor determines horizontal scale 102 and vertical scale 104, respectively for detailed window 30. The processor then displays portion 50, labeled 51 for convenience, in detailed window 30.

Figure 5C:
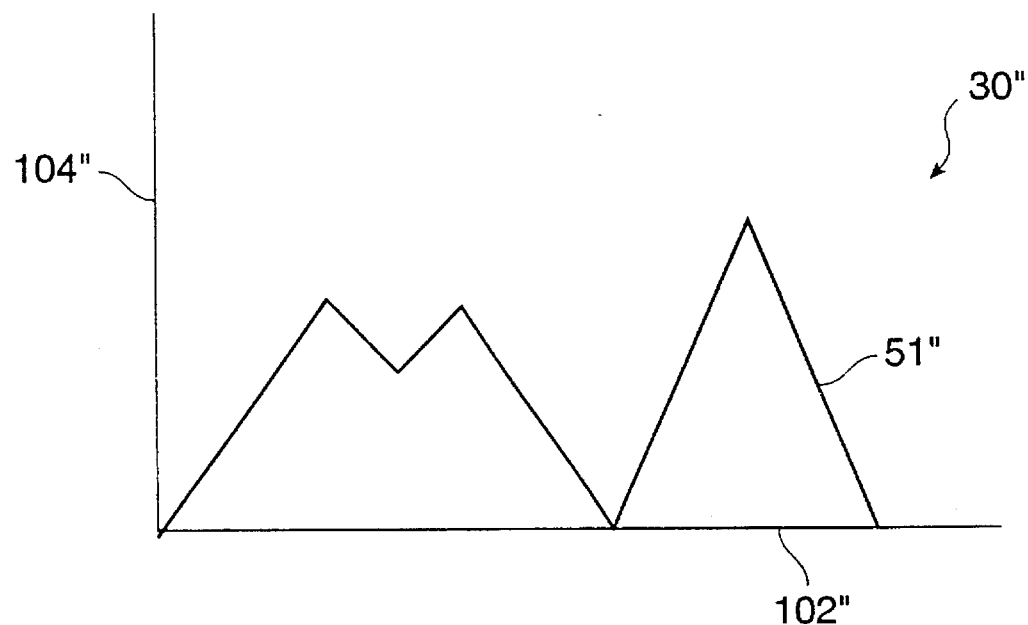
FIG. 5C schematically illustrates the detailed window corresponding to the overlay window at a second position in FIG. 5A.

FIG. 5C illustrates schematically detailed window 30" corresponding to overlay window 20" in FIG. 5A. Detailed window 30" includes a horizontal scale 102" representing a range of wave numbers, a vertical scale 104" representing a range of absorbance values, and portion 51" of spectrum 40.

In a preferred embodiment, the user uses mouse 5 to select overlay window 20" in FIG. 5A, to shift overlay window 20 horizontally and vertically, and to resize horizontal side 102 and vertical side 104 to become overlay window 20". Overlay window 20" on spectrum 40 defines portion 50" of spectrum 40. Based upon the size of horizontal side 22" and the size of vertical side 24" in FIG. 5A, the processor determines horizontal scale 102" and vertical scale 104" respectively for detailed window 30 The processor then displays portion 51" in detailed window 30"

Radar Window of an initial Refinements

Figure 6:
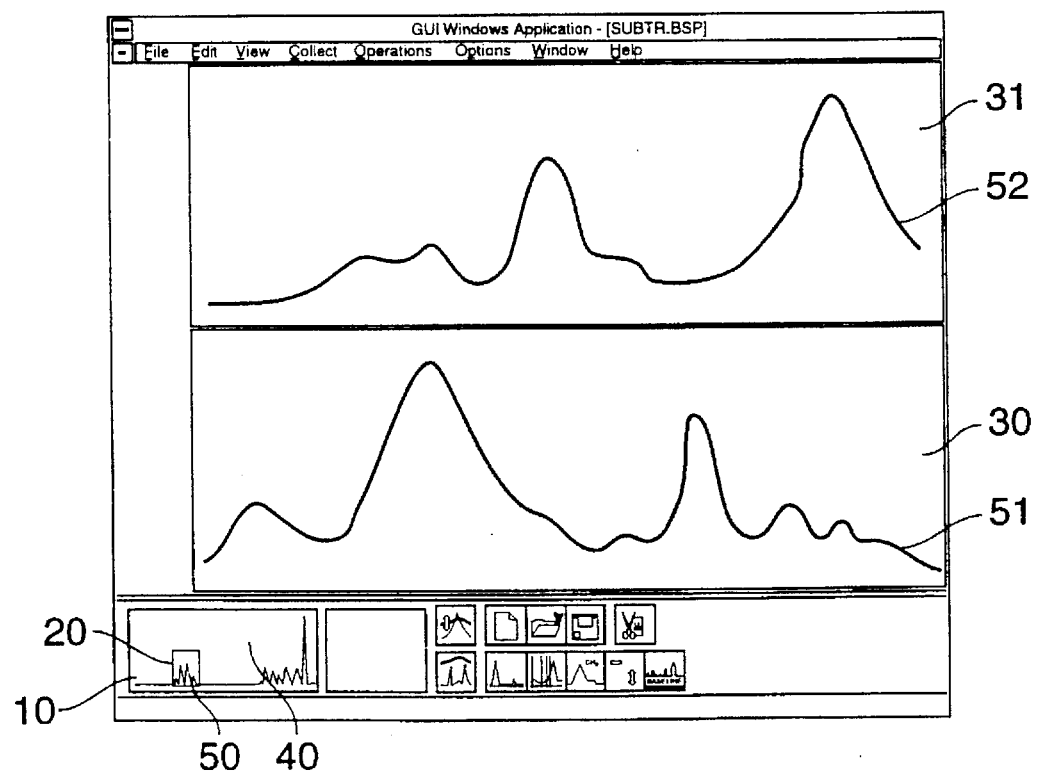
FIG. 6 illustrates a display of another embodiment of the present invention.

FIG. 6 illustrates a display of another embodiment of the present invention. The examples in FIGS. 2 and 5A-5C illustrate the use of one radar window 10 with one detailed window 30 on a display. In a preferred embodiment, however, more than one detailed window is displayed to the user at the same time on the display, such as detailed window 30 and a second detailed window 31. Thus, a typical monitor display includes radar window 10 having an overlay window 20 and detailed windows 30 and 31. Radar window 10 displays a spectrum 40 and overlay window 20 bounds portion 50 of spectrum 40, detailed window 30 displays a portion of spectrum 40 labeled 51, and detailed window 31 displays a portion 52 of a second spectrum (not shown). Spectrum 40 and the second spectrum are displays of spectrum data.

Multiple detailed windows such as 30 and 31 are used, for example, when the user wants to perform a visual comparison of two or more different spectrum at the same time. Although it is possible to have as many radar windows as there are detailed windows on the display, because of the limited display area on monitor 2, in the preferred embodiment, only one radar window 10 is provided.

In the preferred embodiment, radar window 10 displays the spectrum associated with an "active" detailed window and an "active" spectrum. The "active" spectrum is the spectrum upon which the processor can perform operations, such as saving, modifying, etc. To "activate" a spectrum and "activate" a detailed window, the user uses a graphic input device such as mouse 5 and clicks a pointer within one of the detailed windows on the display. In FIG. 6 the "active" spectrum is spectrum 40 and the "active" detailed window is window 30.

The user can override the above described functionality of overlay window 20 by selecting command button 71 or command button 76, illustrated in FIG. 2. Selecting command button 71 automatically re-scales vertical scale 104 such that the vertical range of portion 51 is enhanced, while keeping horizontal scale 102 relatively fixed. Enhancement includes increasing or decreasing the range of absorbance values in vertical scale 104.

Selecting command button 76 automatically re-scales vertical scale 104 and horizontal scale 102 such that the full range of spectrum 40 is displayed in detailed window 30. This includes increasing or decreasing the range of absorbance values in vertical scale 104 and increasing or decreasing the range of wave numbers in the horizontal scale 102. To return to utilizing and manipulating overlay window 20 in radar window 10, the user selects command button 77.

Graphic Manipulation—Subtraction

Subtraction of a reference spectrum from a sample spectrum allows the user to eliminate spectral artifacts from the sample spectrum or to determine the composition of the sample spectrum. The result of the spectral subtraction is a difference spectrum.

Figure 7:
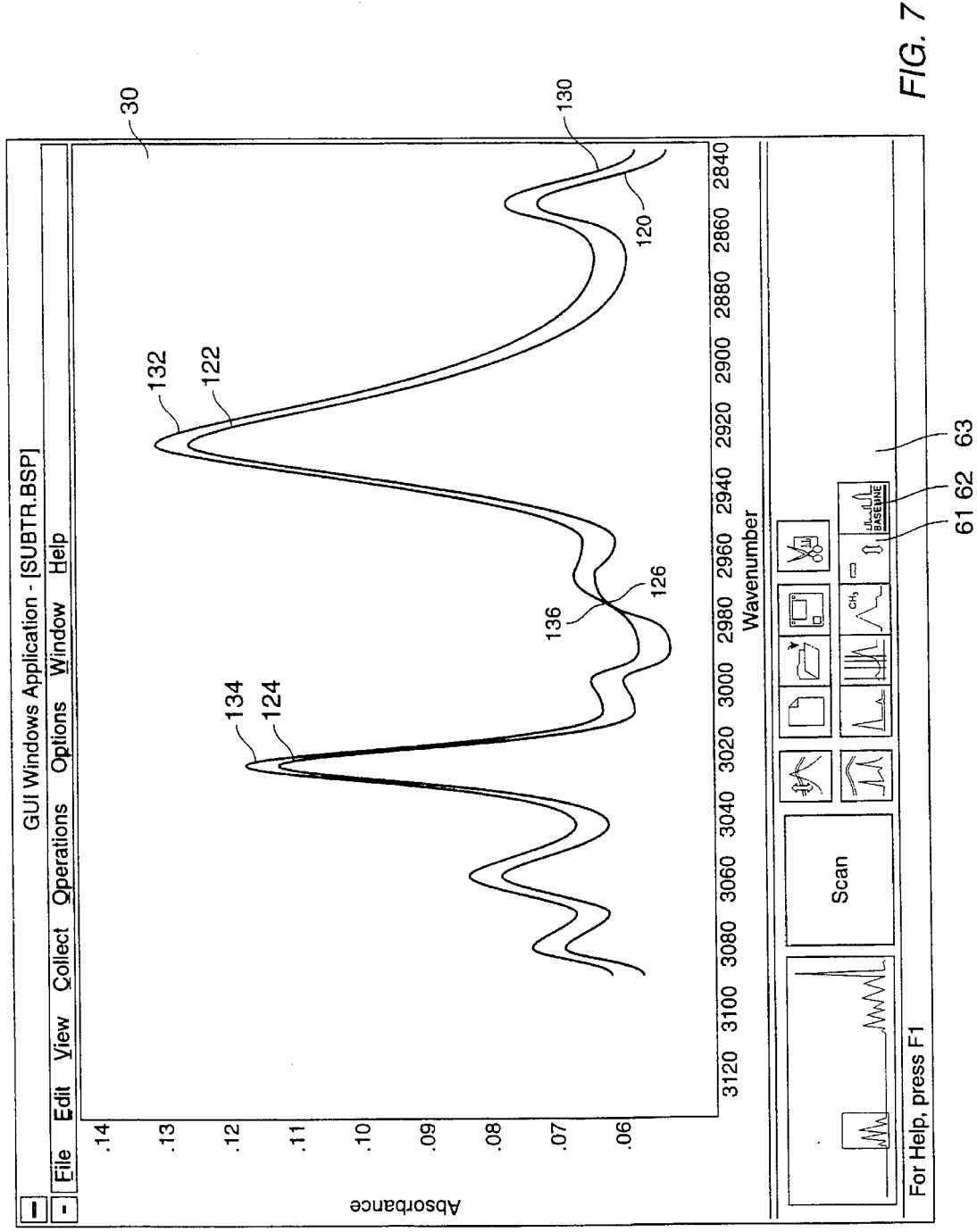
FIG. 7 illustrates the display of a portion of a sample spectrum and a portion of a reference spectrum in a detailed window.

FIG. 7 illustrates the display of portion 120 of a sample spectrum and a portion 130 of a reference spectrum over the same wavenumber range on detailed window 30. These portions 120 and 130 can be displayed in two different user-selected colors to avoid any confusion between the spectra. The wavenumber ranges of the two spectrum are determined by overlay window 20 in radar box 10. Portion 120 includes points 122, 124, 126, and portion 130, includes points 132, 134, and 136. The reference spectrum includes spectral data from known reference materials such as pure compounds and mixtures.

In a preferred embodiment, the user scans a sample spectrum using spectrometer 6 (or retrieves a previously scanned spectrum from disk drive 9) and then selects command button 61 to enter the graphic subtraction mode. Once in the graphic subtraction mode, the user retrieves a reference spectrum from disk drive 9.

Using overlay window 20 in radar window 10 to survey the sample spectrum and the reference spectrum, the user typically determines which portions of the sample spectrum and the reference spectrum appear similar in shape. If the sample spectrum does not have waveform characteristics similar to that of the reference spectrum, the user may decide to skip this reference spectrum and load a new reference spectrum from disk drive 9. If the sample spectrum has similar characteristics to the reference spectrum, the user may decide to perform the graphical subtraction. In the example in FIG. 7, the sample spectrum includes regions surrounding points 122 and 124 which are similar in shape to regions surrounding points 132 and 134 of the reference spectrum, respectively.

Once the user determines a reference spectrum to use for the graphical subtraction, the processor generates a difference spectrum between the two spectrum. The difference spectrum can be displayed in a third user selected color to visually distinguish the difference spectrum from the other spectra.

Figure 8:
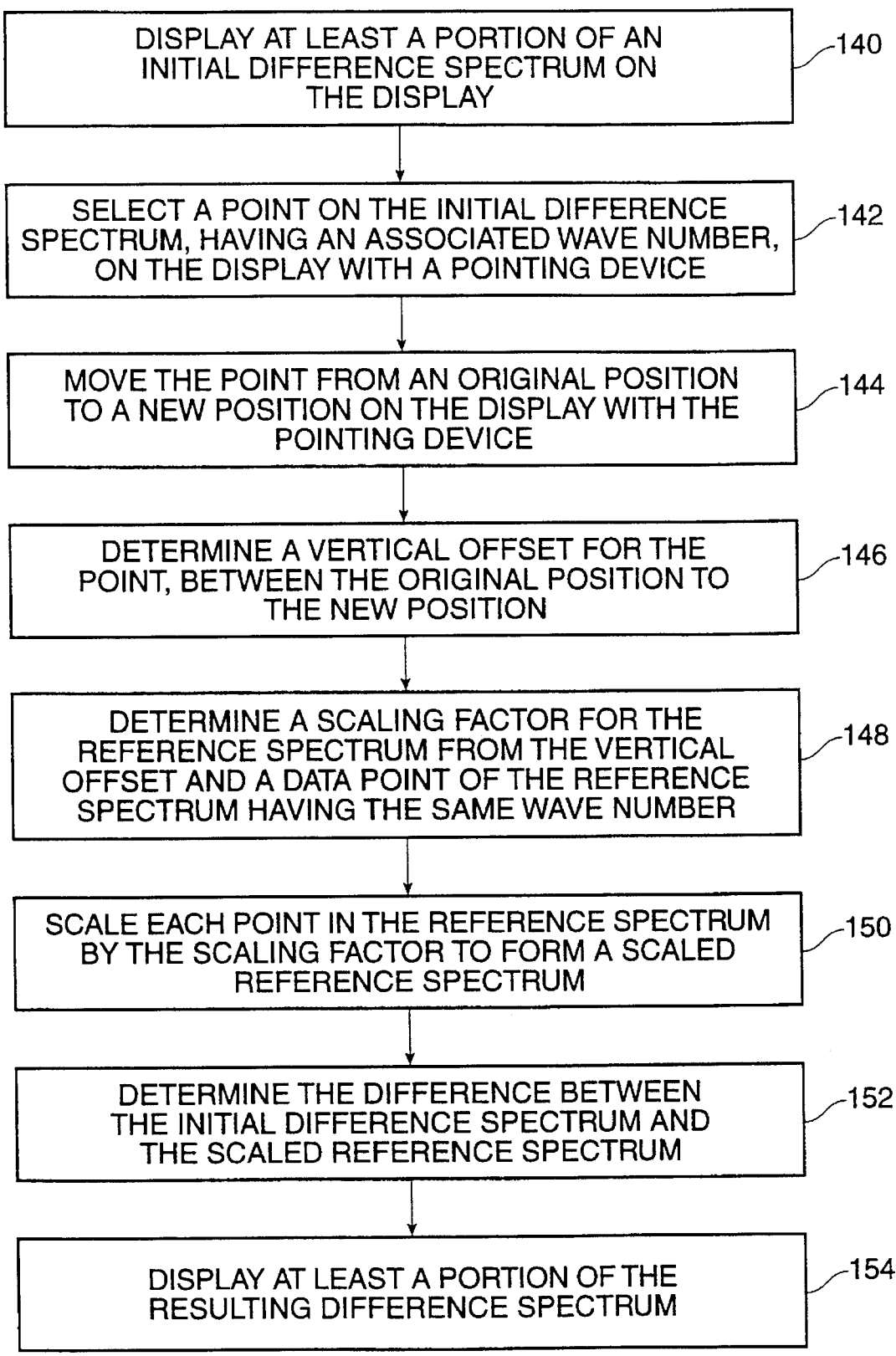
FIG. 8 is a flow diagram of an embodiment of the process of forming a difference spectrum.

FIG. 8 is a flow diagram of an embodiment of the process of forming a difference spectrum. At least a portion of an initial difference spectrum is first displayed to the user on the display (step 140). In a preferred embodiment, the initial difference spectrum is equal to the sample spectrum, i.e., the values of "a" and "b" in equation (1) are zero (0). Alternatively, the initial difference spectrum can be proportional or linearly related to the sample spectrum. The user selects a point on the initial difference spectrum with a pointing device, such as mouse 5 (step 142). The selected point represents a data point in the initial difference spectrum having an absorbance value at an associated wave number. The user moves the point from the original position to a new position, again using mouse 5 in a well known manner (step 144). The processor then determines the vertical offset between the original position and the new position (step 146). In the preferred embodiment the difference in absorbance values between the original position to the new position is represented by the vertical offset.

A scaling factor for the reference spectrum is determined based upon the value of the vertical offset and upon the value of the reference spectrum at the wavenumber of the selected point (step 148). In the preferred embodiment, the scaling factor is the difference in absorbance values divided by the absorbance value of the reference spectrum at the wave number. The reference spectrum is then uniformly scaled by the scaling factor to form a scaled reference spectrum (step 150). In a preferred embodiment, the absorbance value for each data point in the reference spectrum is multiplied by the scaling factor to form the scaled reference spectrum. The processor then determines the difference between the sample spectrum and the scaled reference spectrum (step 152). In a preferred embodiment, for each wave number, the absorbance value for the sample spectrum is subtracted by the absorbance value for the scaled reference spectrum to form the difference spectrum. At least a portion of the resulting difference spectrum is then displayed to the user (step 154), and the resulting difference spectrum will run through the new position of the selected point. The display of the difference spectrum, in a preferred embodiment, serves as immediate feedback to the user of the results of the subtraction process. The user may repeatedly perform steps 140–154 using the difference spectrum in place of the sample spectrum, to further subtract the reference spectrum from the difference spectrum and to form a new difference spectrum.

Figure 9:
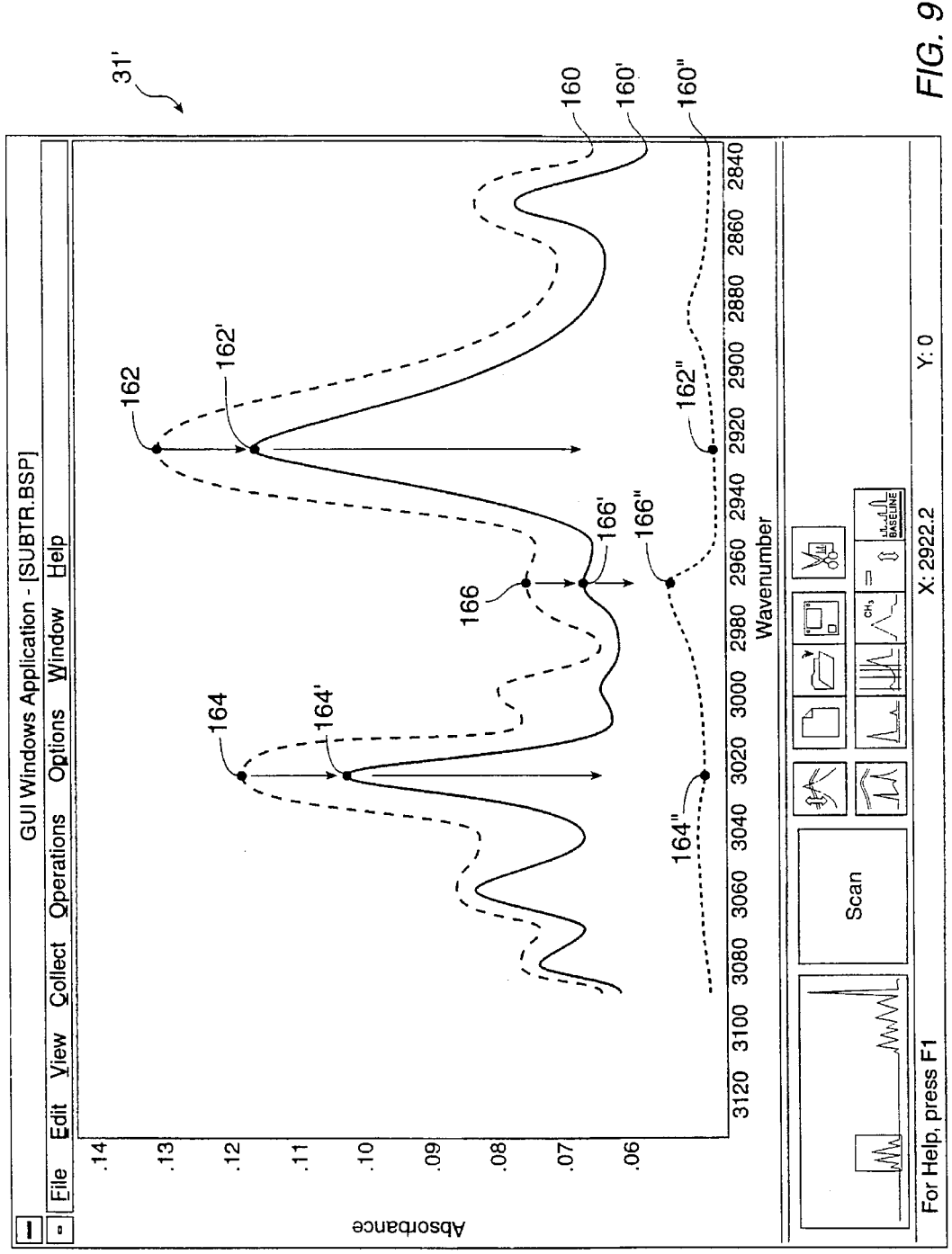
FIG. 9 illustrates a display of a portion of an initial difference spectrum and portions of two representative difference spectrum.

FIG. 9 illustrates a display of a portion 160 of an initial difference spectrum (not shown in its entirety) and portions 160, 160' and 160" of three representative difference spectra (not shown in their entirety) on a detailed window 31'. Portion 160 includes points 162, 164, 166, portion 160' includes points 162' 164' and 166' and portion 160" includes points 162" 164" and 166".

In a preferred embodiment, the initial difference spectrum is set equal to the sample spectrum. The initial difference spectrum is equal to the sample spectrum without the reference spectrum being subtracted. To calculate a new difference spectrum the user uses mouse 5 to select a point on the initial difference spectrum. The user then moves that point vertically on the display. Moving the point on the initial difference spectrum vertically is equivalent to subtracting a scaled percentage of the reference spectrum from the sample spectrum.

Portion 160 illustrates an initial difference spectrum. When a user selects and drags point 162 to point 162' for example, Portion 160 is erased and portion 160' is displayed to the user. Of course multiple intermediate difference spectra are also displayed to the user as the user moves from 162 to 162'. These are not shown, for clarity. The user continues dragging data points until the user is satisfied with the difference spectrum, for example, 160".

FIG. 9 illustrates the result of the user dragging point 162 of portion 160 to point 162' and onto point 162". In a preferred embodiment, only one difference spectrum is displayed to the user at a time, e.g., 160, 160' or 160" In response to the vertical offset between point 162 to 162' and onto 162", the processor calculates the remaining points in the difference spectrum, as illustrated by portion 160' and 160". In a preferred embodiment, setting the baseline compensation factor "b" in equation (1) to zero simplifies equation (1) to equation (2).

$$Z=S-(a*R) \qquad (2)$$

In equation (2), Z represents the difference spectrum, S represents the sample spectrum, R represents the reference spectrum, and "a" is the scaling factor for the reference spectrum. In FIGS. 7 and 9, the value of point 162' corresponds to Z, the point 162 corresponds to S, and point 132 corresponds to R for a given wave number. Since the processor knows the values for Z, S, and R, the processor calculates a corresponding value for "a" based upon point 122'. Using this value for "a" and knowing the values of the sample spectrum S and reference spectrum R for the remaining wave numbers, the processor then calculates the remaining values for the difference spectrum Z for all the remaining wave numbers.

In FIG. 7, for example, point 122 has an absorbance of about 0.132 and point 132 has an absorbance of about 0.137, and in FIG. 9, point 162' has an absorbance of about 0.102. Using equation (2) with Z=0.102, S=0.132, and R=0.137, the scaling factor "a" is calculated to be about 0.219.

Using 0.219 for "a" in equation (2), the processor then calculates the difference spectrum for each of the remaining points from the sample spectrum. For example in FIG. 7, point 124 has an absorbance of about 0.119 and point 134 has an absorbance of about 0.125. Using equation (2) with S=0.119, "a"=0.219 as calculated above, and R=0.125, the value of point 164' is calculated to be about 0.916. Point 164' in FIG. 9 is thus set to 0.916. In a preferred embodiment, the described sequential operations appear continuous.

The user may, alternatively to graphic subtraction, directly select a value for "a" by commonly used techniques such as entering text in a dialog box, or scrolling through a list of values of "a" with up and down arrows on the display.

In a preferred embodiment, the user graphically manipulates points upon the difference spectrum, until satisfied that difference spectrum does not include any contributions from the reference spectrum. As seen in FIG. 9, once the absorbance of the difference spectrum has reached a relatively constant value, the user identifies remaining points such as point 166". Point 166" may represent another chemical component in the sample spectrum, for example.

The difference spectrum can be displayed and manipulated in its own window with the sample spectrum and the reference spectrum in another window, for example window 31 and 30, respectively, as in FIG. 6. Alternatively, all three spectrum can be displayed in a single window.

The user repeats the above graphic subtraction procedure with a new reference spectrum from a library of reference spectrum in order to identify any remaining components or to remove other artifacts on the difference spectrum.

Spectral Searching

FIG. 10 illustrates the result of searching the sample spectrum in FIG. 2 against a library of known spectrum. The results, stored in component box 170 are displayed to the user and can be saved to memory. Component box 170 includes a name column 172, a spectrum column 174, and a structure column 176.

In the preferred embodiment, the processor automatically compares the sample spectrum to a library of reference spectrum stored in disk drive 9 to determine the composition of the sample spectrum. The processor determines the composition according to well known algorithms known to one skilled in the art.

In a preferred embodiment, after determining the composition of the sample spectrum, the processor displays the name of the reference samples matched, a full scale view of the reference spectrum, and displays the chemical structure. In FIG. 10, the samples are stored in name column 172, the reference spectrum for the chemicals are shown in spectrum column 174, and the structure of the chemicals are shown in structure column 176.

Graphic Manipulation—Baseline Offset Correction

Baseline Offsets are used to compensate for offsets in absorbance values due to artifacts during collection of the sample spectrum or due to artifacts in subtracting reference spectrum. If an offset is relatively constant throughout out the range of wave numbers of the sample spectrum, the value of "b" in equation (1) can be set to a constant to correct the offset. However, if an offset is non-uniform throughout the range of wave numbers of the sample spectrum, the user can define a baseline offset as a function of wavenumber to correct the offset. When correcting only the baseline offset, the value of "a" in equation (1) is preferably set to zero and the value of "b" is modified.

In a preferred embodiment the user directly sets the value of "b" in equation (1) to a constant in two ways. First, when in graphic subtraction mode, the user can directly select a value for "b" by commonly used techniques such as entering text in a dialog box, or scrolling through a list of values of "b" with up and down arrows on the display (while "a" is held constant). Second, when in a baseline correction mode, the user can graphically set the value of "b" to a constant. The user enters the baseline correction mode by selecting command button 62.

FIGS. 11 and 12 illustrate the definition of a portion of a baseline offset (not shown) as a function of wavenumber and the resulting spectrum. The baseline offset includes line segments 180 and 182 and curved segment 184.

In a preferred embodiment, the user directly sets the value of "b" in equation (1) as a function of wavenumber while in the base line correction mode. In operation, the user graphically defines the shape of the baseline offset in relation to the wavenumber with mouse 5. Using well known graphic manipulation techniques from computer drawing programs, the user can define line or curved segments by defining the appropriate parameters as shown as line segments 180 and 182 and as curved segment 184. In a preferred embodiment, immediately after editing the graphic baseline offset, the sample spectrum is updated to reflect the new baseline offset. This is illustrated in FIG. 12 with the baseline correction of FIG. 11 of the sample spectrum in FIG. 2.

Graphic Manipulation Based upon Regions of Interest

Regions of Interest (ROI) are areas in a spectrum upon which the processor utilizes spectrum data for operations.

FIG. 13A illustrates a display of a portion 190 of a spectrum on detailed window 30. Portion 190 is a portion of the difference spectrum including a region of interest (ROI) 200.

In operation, selecting command button 78 in FIG. 2 allows the user to define an ROI. The user defines an ROI by first delineating a wavenumber range of the spectrum and choosing whether the delineated range is the ROI, or the spectrum outside the delineated range is the ROI.

In a preferred embodiment, without an ROI 200, spectral searching of a sample spectrum and a reference spectra is calculated based upon the entire range of wave numbers as illustrated in FIG. 11. In a preferred embodiment, with an ROI 200, spectral searching is calculated based only upon the range of wave numbers in the defined ROI 200. The spectral searching occurs over the entire wavenumber range as without ROI 200, however, ROI 200 is the only region from which the processor analyzes data. An application where an ROI is used is when the composition of only a certain portion of the sample spectrum is of interest.

FIG. 13B illustrates the result of an spectral searching based upon ROI 200. In contrast to the result of the spectral searching in FIG. 10, the spectral searching in FIG. 13B results in locating only a particular substance.

Other Features

FIG. 14 illustrates retrieving a previously scanned sample spectrum from disk drive 9. A dialog box 200 includes a file box 210 a text entry box 220, a preview box 230, and a retrieve button 240.

In a preferred embodiment, the user selects buttons 73 or 74 to open dialog box 200 on display 2. The list of files, directories and drives, either local or on a network accessible machine, is displayed in file box 210. The user selects a file to retrieve from the list of files in file box 210 by using a graphical input device, such as mouse 5, and pointing and clicking upon the file name. Alternatively, the user selects a file to retrieve by typing a file name into keyboard 4, after first selecting text entry box 220 with mouse 5. A preview of the user selected file is displayed in preview box 230 when the user clicks upon the file name, or enters a file name into text entry box 220. Once the user is satisfied with the file selection, the user retrieves the spectrum data by pointing and double clicking upon the file name with mouse 5, or clicking upon retrieve button 240.

In a preferred embodiment, a file (or document) contains data (a spectrum) for a sample or a reference, or a series of spectra, or spectra from different samples, or spectra processed in different ways, plus other information related to the spectrum. This typically includes data from an experiment, an individual's work, a series of related experiments, a day's worth of work, a project, etc.

The presentation of the document by the software is in one window. A moveable "window shade" line separates the window into two portions: one containing a large area for the presentation of spectra and the second containing a spreadsheet. Each row in the spreadsheet contains cells displaying values corresponding to a single spectrum, possibly including but not limited to properties such as the name of the spectrum, the spectrum trace itself, text information about the sample or spectrum, the chemical structure of the material, etc. Each column of the spreadsheet is dedicated to a particular spectrum property. The selection of spreadsheet columns is configurable.

To modify or view a document, the user is given the ability to manipulate the data in a manner similar to spreadsheets. A typical display of a document displays the names of the spectra traces in one column of the document, the actual spectra traces in another column of the document, the properties of the underlying samples in another column of the document and other graphic information in yet another column of the document. One example of a view of a document is illustrated in FIG. 10. Graphic information includes chemical structures as illustrated in column 176 of FIG. 10.

The interface allows the user to access an individual spectrum trace, ranges of particular spectra traces, or groups of spectra traces in a document or between documents, and allows the user to align or register spectra traces that span different ranges. The interface also allows the user to choose which columns of a document to display at any one time. Such a choice is variable between documents and between applications.

The ability to align spectra traces is important where a series of traces are displayed in a spreadsheet column having similar data points (e.g. wavenumber), whether or not the spectra have common range. In one embodiment, all spectra in a spreadsheet with common X axis units are displayed in the full range. In another embodiment, clicking in a spectrum's trace display cell selects a spectrum, causes it to be shown to the full extent of its data range, and causes all other spectra traces to display data from within the same range. For example, if a first spectrum has a wavenumber range from 3300 to 1800, even though a second spectrum has a wavenumber range from 3600 to 1600, only the range of wavenumbers from 3300 to 1800 are displayed. Alternatively, in another embodiment, the displays of spectra are re-scaled to show the full range of the respective spectra, using the same X axis unit spacing ratio as the selected spectrum. For example, using the example above, if the first spectrum is displayed at a ratio of 1500 wavenumbers per three inches on a display, the second spectrum will occupy four inches on the display, i.e. a ratio of 500 wavenumbers per inch.

Figure 16:
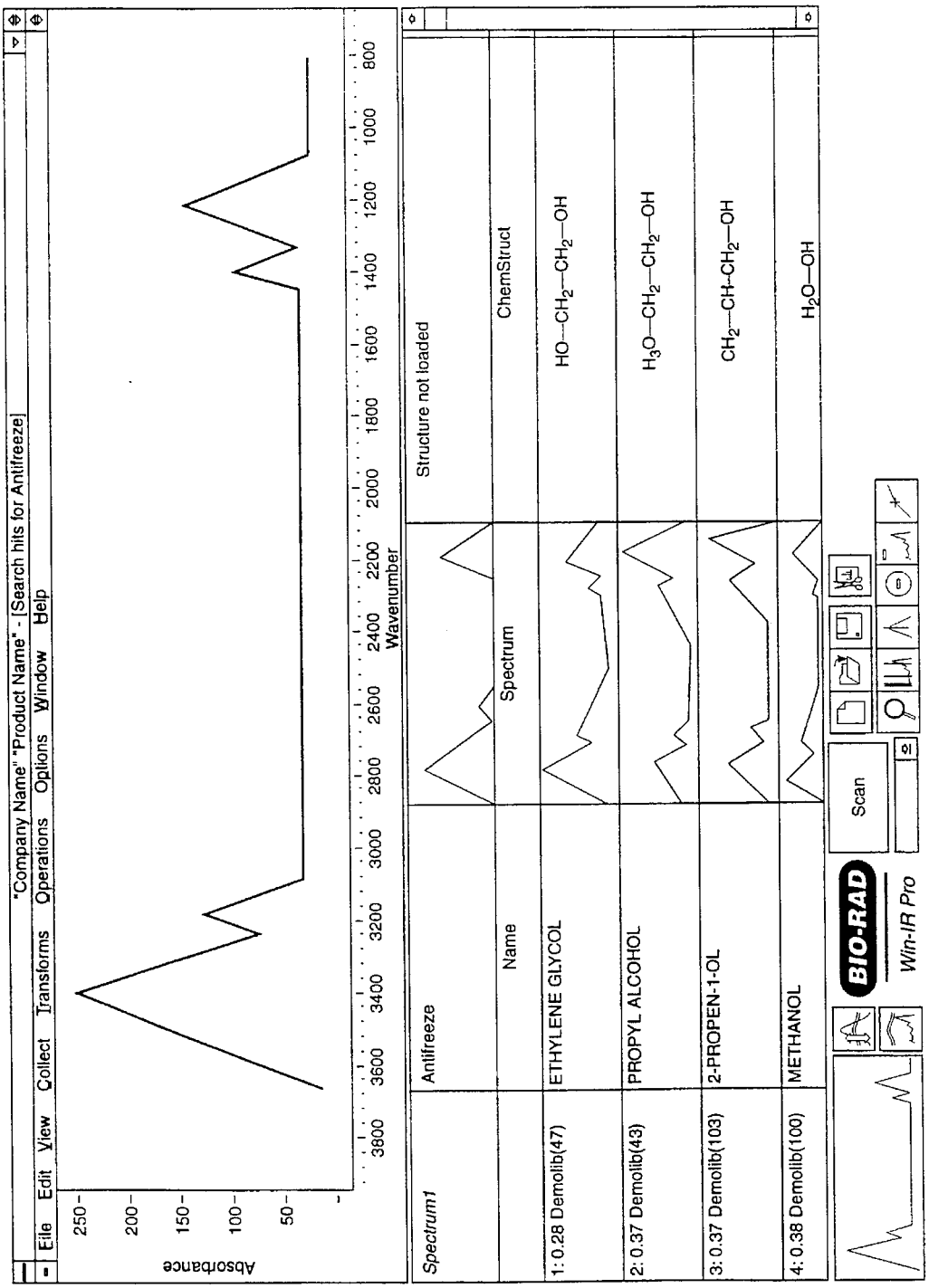
FIG. 16 illustrates a document containing a spectral library that includes names and index information for the spectrum, the actual spectrum, and properties and structures of the compounds.

Examples of the information stored in documents include:

1) A document containing a spectral library that includes names and index information for the spectra, the actual spectra, and properties and structures of the compounds. This is illustrated in FIG. 16.

Figure 17:
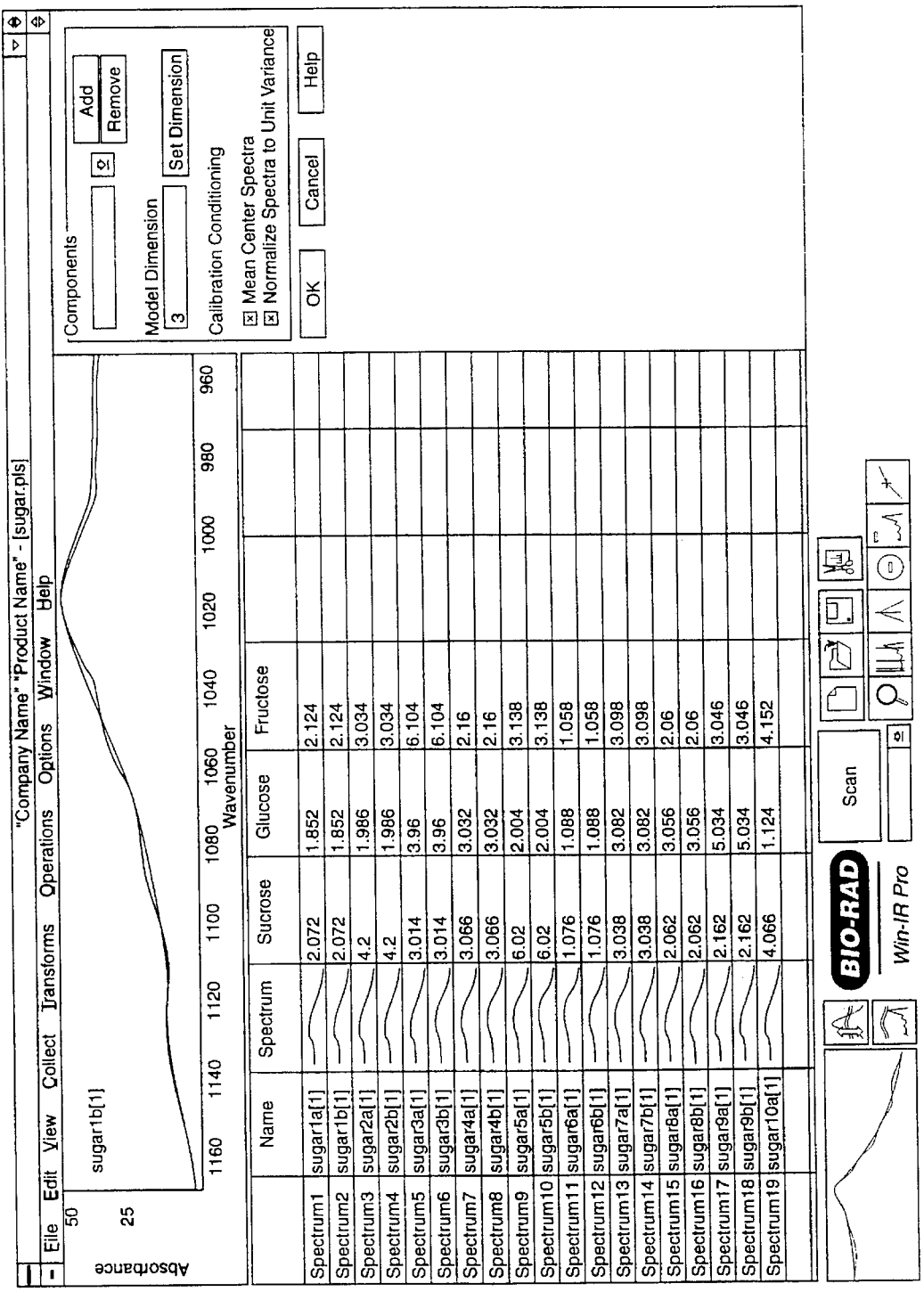
FIGS. 17 and 18 illustrates a document containing a collection of spectrum used to set up and calibrate quantitative analysis.
Figure 18:
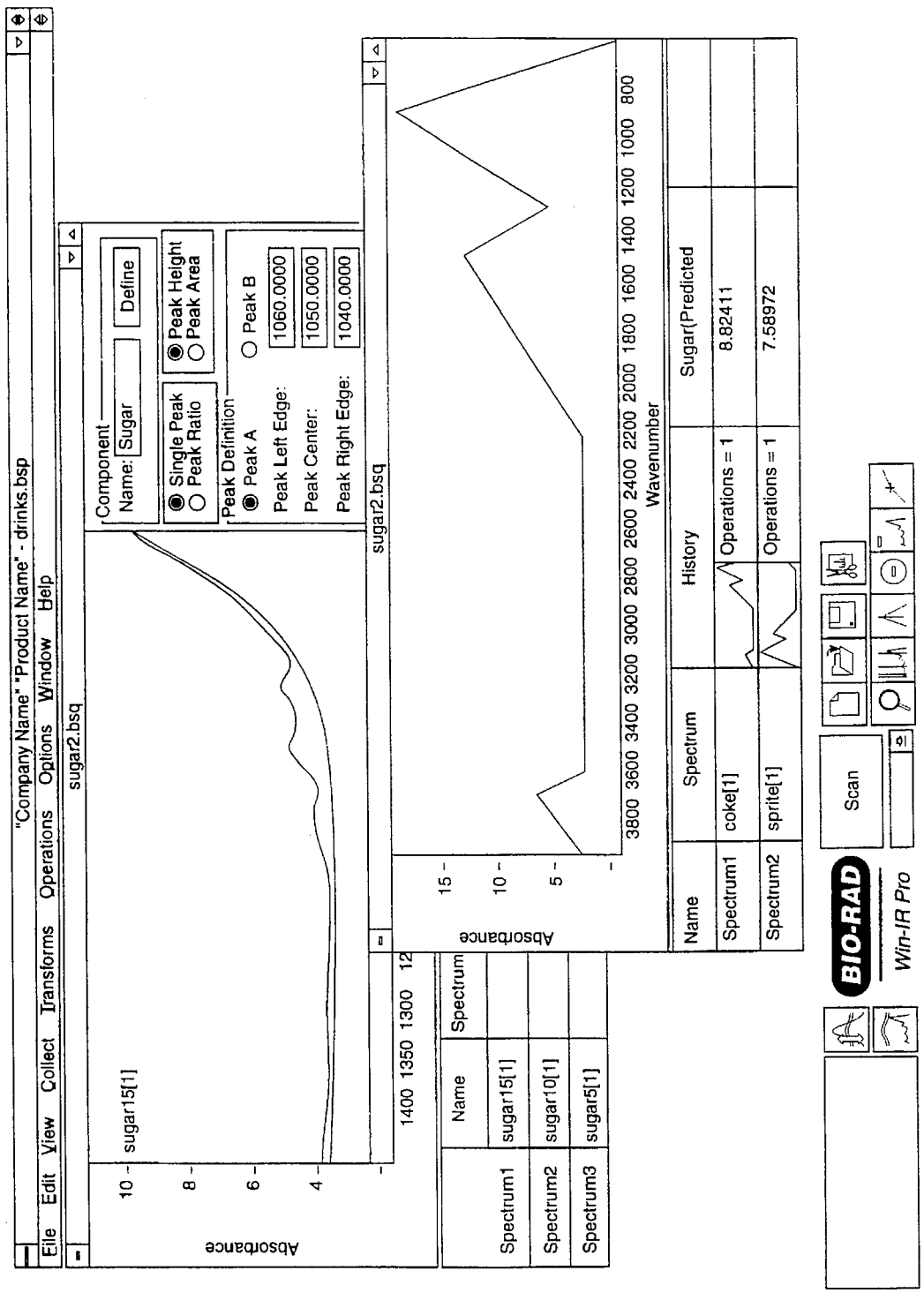

2) A document containing a collection of spectra used to set up and calibrate quantitative analysis. For example, a document that contains the actual spectra of the specimens, the names of the components present in each specimen, the concentrations of those components in each specimen, the portion(s) of the spectra to be used in the calibration and analysis, the style of analysis (e.g. band height measurement, partial least squares analysis), and the resulting calibration data. This is illustrated in FIG. 17 and FIG. 18.

Figure 19:
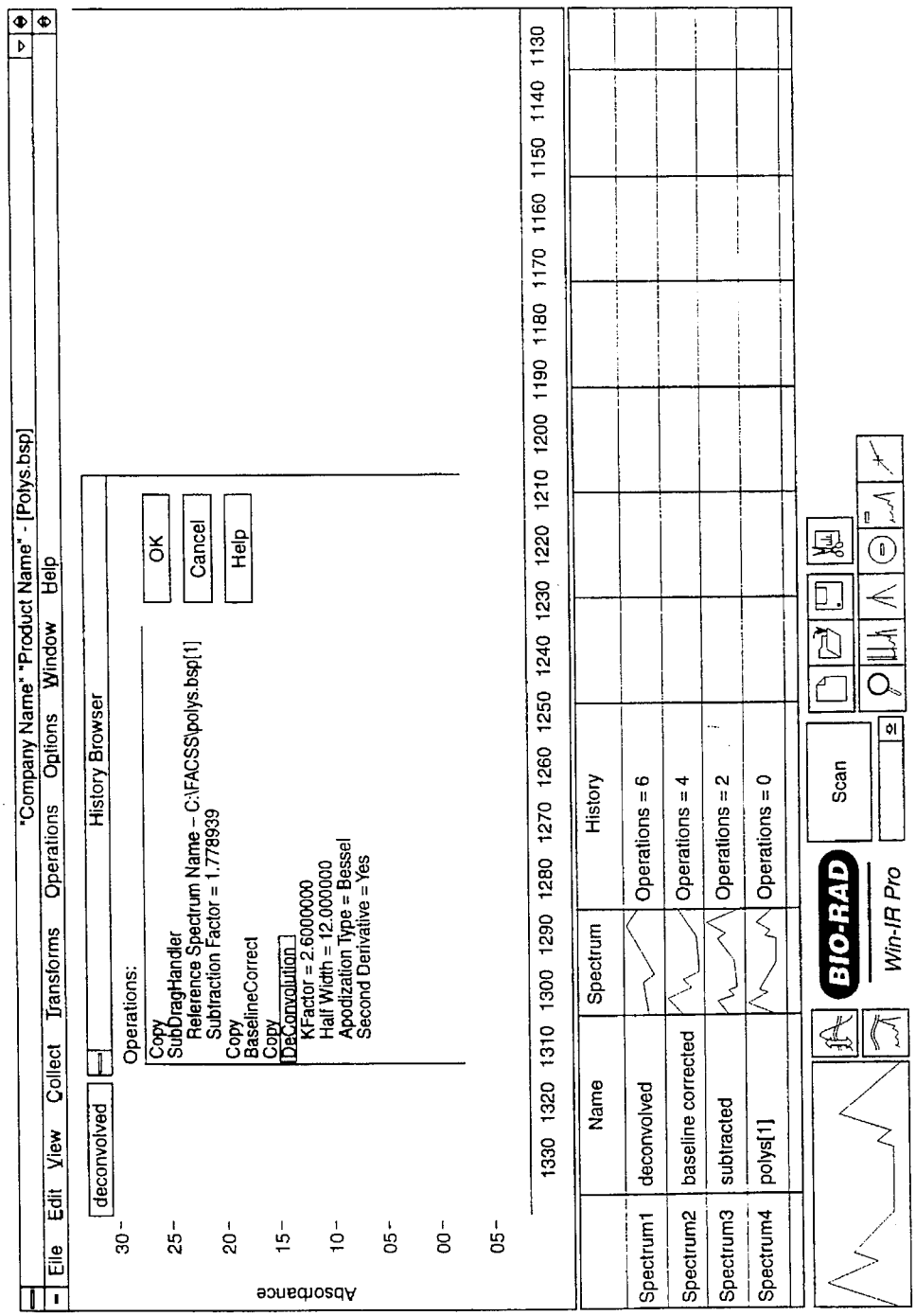
FIG. 19 illustrates a document containing a processing history.

3) A document containing a collection of spectra to be analyzed. For example, a document that contains spectra to be analyzed, the resulting components and component concentration present in each spectrum, the method used for the analysis, and the processing history. This is illustrated in FIG. 19.

4) A document containing a set of spectra from an infrared mapping experiment. For example, spectra that are associated with coordinates from which the spectra were obtained, and data obtained from the set of spectra that produce infrared-based maps of the specimen.

5) A document containing a set of spectra collected under varying conditions. For example, different experimental conditions and the associated data. Conditions include those internal to the spectrometer (e.g. resolution, number of scans), and external to the spectrometer (e.g. temperature of the specimen, pressure). Alternatively, the software may itself control those conditions.

Figure 20:
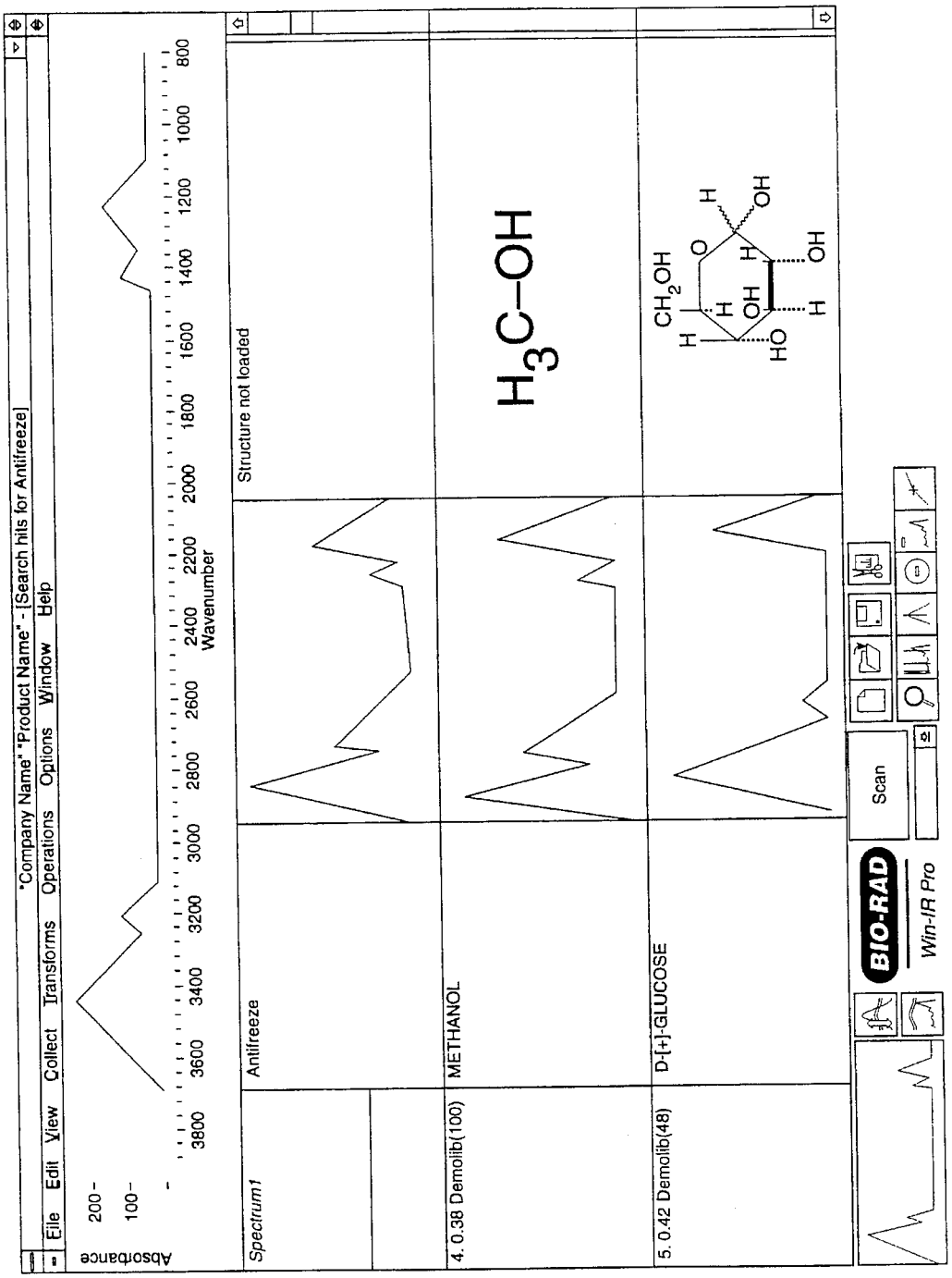
FIG. 20 illustrates a document containing the results of a spectral search.

FIG. 20 illustrates a document containing the results of a spectral search.

FIG. 15 illustrates a peak mode and a clipboard window. As will be described below, the peak mode allows the user to quickly obtain characteristics of a selected peak while the clipboard window allows the user to copy a selected portion of a spectrum.

In a preferred embodiment, selecting command button 79 in FIG. 2 enters the system into a "peak" mode. In peak mode the user uses mouse 5 to select a point such as point 53 on partial spectrum 51. In response to the selection, the processor automatically determines characteristics of the closest peak, such as peak 54. These characteristics can include the maximum and minimum absorptions of the peak, the wavenumber of the peak, the area of the peak, the range of wave numbers for the peak.

Selecting command button 75 in FIG. 2, activates clipboard window 250. Using mouse 5, the user defines the size and location of clipboard window 250 on detailed window 30. The manipulations are similar to those for sizing and positioning the overlay window in the radar window. Clipboard 250 bounds portion 260 which the processor then copies into a "clipboard" that other computer programs can access.

Conclusion

In the foregoing specification, the invention has been described with reference to a specific exemplary embodiments thereof. Many changes or modifications are readily envisioned. For example, changing the graphical manipulation from that of equation (1), changing the effect of the graphical manipulation based upon direction of movement, and including further functional buttons on the display, among other changes, are included within other embodiments of the present invention.

The specification and drawings are, accordingly, to be regarded in an illustrative rather than in a restrictive sense. It will, however, be evident that various modifications and changes may be made thereunto without departing from the broader spirit and scope of the invention as set forth in the claims.

What is claimed is:

1. A method for graphically forming a difference spectrum from a sample spectrum and a reference spectrum on a computer system, the computer system including a display, a processor, a memory, and a relative pointing device, the method comprising the steps of:

displaying at least a portion of an initial difference spectrum on the display, said initial difference spectrum being proportioned to the sample spectrum.

selecting a data point in said initial difference spectrum, having an associated wave number, on the display with the relative pointing device;

moving said data point a measurable amount on the display with the relative pointing device;

determining a scaling factor in response to said measurable amount and to a data point in the reference spectrum having said associated wavenumber with the processor;

scaling each data point in the reference spectrum by said scaling factor to form a scaled reference spectrum;

determining the difference spectrum between the sample spectrum and said scaled reference spectrum with the processor; and displaying at least a portion of the difference spectrum on the display.

2. The method of claim 1, wherein said step of moving said data point comprises:

moving said data point from an original position to a new position on the display with the relative pointing device; and determining said measurable amount between said new position and said original position.

3. The method of claim 2, wherein said measurable amount comprises a vertical offset on the display.

4. The method of claim 1, further comprising the step of displaying at least a portion of the reference spectrum on the display.

5. The method of claim 1, wherein said initial difference spectrum equals the sample spectrum.

6. A method for graphically forming a difference spectrum from a sample spectrum and a reference spectrum on a computer system, the computer system including a display, a processor, a memory, and a relative pointing device, the method comprising the steps of:

displaying at least a portion of an initial difference spectrum on the display, said initial difference spectrum linearly related to the sample spectrum, selecting a data point in said initial difference spectrum, having an associated wave number, on the display with the relative pointing device;

moving said data point from an original position to a new position on the display with the relative pointing device;

subtracting said new position from said original position to determine a vertical offset;

dividing said vertical offset by a data point in the reference spectrum having said associated wavenumber to determine a scaling factor for the reference spectrum;

scaling the reference spectrum by said scaling factor to form a scaled reference spectrum;

subtracting said scaled reference spectrum from the sample spectrum to form the difference spectrum; and displaying at least a portion of the difference spectrum on the display.

7. The method of claim 6, wherein said initial difference spectrum equals the sample spectrum.

8. A method for forming a spectrum graphically from a sample spectrum on a computer system, the computer system including a display and a graphical input device, the method comprising the steps of:

displaying at least a portion of an initial spectrum on the display, said initial spectrum being equal to the sample spectrum; and displaying at least a portion of the spectrum on the display, the spectrum being a mathematical combination of the sample spectrum and a scaled reference spectrum, said scaled reference spectrum being a reference spectrum scaled by a scaled value, said scaled value generated in response to graphical manipulation of said initial spectrum by the graphical input device.

9. The method of claim 8 wherein said mathematical combination is a mathematical subtraction.

10. The method of claim 9 wherein said scaled value is positive.

11. The method of claim 8 wherein said reference spectrum contains baseline offset data.

12. A method for graphically manipulating a difference spectrum on a computer system, the computer system including a display and a graphical input device, the method comprising the steps of:

displaying at least a portion of the difference spectrum on the display, the difference spectrum being a mathematical difference between the sample spectrum and a scaled reference spectrum, said scaled reference spectrum being a reference spectrum scaled by a scaled value;

determining an updated scaled value in response to graphical manipulation of the difference spectrum by the graphical input device;

forming an updated scaled reference spectrum from the reference spectrum in response to said updated scaled value; and displaying at least a portion of an updated difference spectrum on the display, said updated difference spectrum being the mathematical difference between the sample spectrum and said updated scaled reference spectrum.

13. The method of claim 12 wherein said scaled value is zero.

14. The method of claim 12 wherein the spectrum contains infra-red spectrum data.

* * * * *